United States Patent [19]
Pier

[11] Patent Number: 5,277,904
[45] Date of Patent: Jan. 11, 1994

[54] BROAD SPECTRUM DERMATOPHYTE VACCINE

[76] Inventor: Allan C. Pier, P.O. Box 3806, Laramie, Wyo. 82071

[21] Appl. No.: 603,554

[22] Filed: Oct. 26, 1990

[51] Int. Cl.$^5$ .............................................. A61K 39/00
[52] U.S. Cl. ..................................... 424/88; 435/171; 435/240.46; 435/242; 435/254.1; 435/911
[58] Field of Search ............. 424/88; 435/171, 240.46, 435/242, 254, 911

[56] References Cited
U.S. PATENT DOCUMENTS 4,368,191  1/1983  Sarkisov et al. ...................... 424/88

OTHER PUBLICATIONS

Wawrzkiewica et al, *Biological Abstracts*, vol. 90(8), Reference No. 87115, 1989.
Propost et al, *Infection and Immunity*, vol. 20, pp. 136–141, Apr. 1978.

*Primary Examiner*—Michael G. Wityshyn
*Assistant Examiner*—Abdel A. Mohamed
*Attorney, Agent, or Firm*—Rothgerber, Appel, Powers & Johnson

[57] ABSTRACT

A vaccine for the prophylaxis of dermatophyte infection in animals, such as guinea pigs, cats, rabbits, horses and lambs comprising a suspension of killed *T. equinum, T. mentagrophytes* (var. granulare), *M. canis* and *M. gypseum* in an effective amount combined with an adjuvant. The vaccine of the invention contains advantages over prior art dermatophyte vaccines in that it reduces the risk of infection in inoculated animals and persons utilizing the vaccine and provides cross-immunity.

7 Claims, No Drawings

BROAD SPECTRUM DERMATOPHYTE VACCINE

BACKGROUND OF THE INVENTION

The present invention relates to the vaccination of cats, dogs, livestock and fur-bearing animals against contagious infections caused by dermatophytes. A novel, broad spectrum vaccine has been prepared comprising a suspension of mycelial elements and spores of four "killed" dermatophytes (*Trichophyton equinum, Trichophyton mentagrophytes* (var. granulare), *Microsporum canis* and *Microsporum gypseum*) along with an adjuvant (i.e., immunologic stimulator) that enhances the vaccine's effectiveness. The vaccine is effective in the prophylaxis of infections resulting from the animal's contact with *T. equinum, T. mentagophytes, M. canis,* and *M. gypseum,* major dermatophytic pathogens of animals. Cross immunity against *T. verrucosum* and *M. equinum* is also stimulated by this vaccine.

A. Field of the Invention

Dermatophytoses are contagious, infectious diseases of man and other mammals caused by a group of keratinophilic, parasitic fungi known as "dermatophytes." Although they are not debilitating or fatal, dermatophytoses are among the most prevalent of human and animal infectious diseases. Millions of adults and children in the United States suffer from one or more types of dermatophyte infection. The dermatophytes that characteristically infect animals (i.e., zoophilic dermatophytes) are highly contagious; they persist in the environment as infectious spores for years, and they often transfer from infected animals to their human attendants as zoonotic infections. As a result, they constitute a substantial public health hazard.

Dermatophyte infections can affect various keratinized tissues, such as the hair and *stratum corneum* of the skin causing areas of hair loss, scaliness and cutaneous inflammation. The most frequent dermatophyte infection in animals is called "ringworm" (i.e., infections of the skin or hair); the most frequent dermatophyte infection in man is "athlete's foot" (i.e., infections of that appendage). These diseases are a consequence of the host animal's reaction to the dermatophyte as well as the invasion of the animal's tissues by the fungus. Although the disease can generally be treated, treatment may take weeks or months to completely resolve the condition. Ringworm is unsightly, at best, and in severe cases can result in the generation of disfiguring scar tissue. It has been estimated in recent years that approximately $150,000,000 is spent annually in the United States on the treatment of ringworm.

Ringworm infections in humans and animals can be caused by a number of dermatophytes that reside on various animals, including pets such as dogs and cats, fur-bearing animals (e.g., rabbits and mink) and livestock, such as horses, cattle and pigs. Hair and other skin fragments or debris infected with dermatophytes are lost by infected animals and contaminate the premises where these animals are maintained. Contamination may last for as much as four years. People, such as handlers, who come in contact with the animals or the premises can become carriers for the fungus to other animals or humans. Because ringworm is a world-wide problem and is transmitted between animals and man, the World Health Organization has attempted to diminish the contacting of viable dermatophytes by persons handling animals through reduction of the incidence of infection in animal populations.

In addition to the health consequences to man, the incidence of dermatophyte infections in animals can cause serious consequences for animal owners. Animals infected with dermatophytes are excluded from the sale or show ring and from competitive events, such as horse races. Because dermatophyte infections spread rapidly among animals, entire herds, kennels or stables full of animals may be involved when infection in one or more animals is observed. In animals bred for their meat, infection with dermatophytes may result in a diminished rate of weight gain. Although griseofulvin administered orally or as a feed additive may be used to treat certain types of infected animals, it can be prohibitively expensive where an entire herd is involved, and it may also raise concerns if the animals are used to supply meat or dairy products for human consumption.

In particular, ringworm on cats and dogs caused by *M. canis* and other dermatophytes is a highly contagious infection among those animals and is readily transmissible to humans. Dermatophytoses is easily transmitted by the movement of infectious hair or scales directly from one animal to another or through intermediate contact with physical items, such as wooden fixtures, grooming brushes, carpets, bedding and any other physical items of common contact. Transmission is especially accelerated by wild or stray cats, dogs and rodents that come into contact with household pets. Pedigreed cats and dogs and livestock infected by dermatophytoses are banned from show arenas and may be barred from crossing state or international boundaries. It is important both to the owners of those animals and to the public at large to control dermatophytoses in these animals.

B. Description of the Prior Art

Because dermatophytes are wide spread parasitic agents and because infection eventually engenders acquired immunity in affected individuals, prophylactic use of immunizing agents is indicated to reduce the susceptibility of animals and humans to infection. It is recognized, however, that:

[n]o subject in the field of medical mycology has evoked more controversy than "immunity and resistance" in dermatophyte infections. The voluminous literature begins in the early nineteen hundreds and continues to accumulate unabated to the present day .... There is no single, clear-cut mechanism that will explain all aspects of susceptibility and immunity to dermatophyte infection. (Rippon, "Medical Mycology: the Pathogenic Fungi and the Pathogenic Actinomycetes," W. B. Saunders Company (3rd Ed. 1988), p. 231.)

As reported in Rippon, immunization by injection of live or killed fungi, their extracts, or their metabolic products has been attempted many times in animals. However, the author notes that the challenge with a homologous organism results only in attenuation of the disease. Resistance is transitory only, and complete susceptibility returns after a few months. Rippon's conclusions appear to be based in whole or in part on A. W. Lepper, "Immunological Aspects of Dermatomycoses in Animals and Man," *Rev. Med. Vet Mycol.,* 6:432–42 (1969), which itself is a review of the literature on dermatophyte immunity. See also, S. F. Grappel, "Immunology of Dermatophytes and Dermatophytosis," *Bacteriological Reviews*, 38:222-50 (1974).

Prior to the present invention, there has been no commercially practicable vaccine for the prevention of ringworm in dogs, cats, livestock and fur-bearing animals. Prophylaxis of *T. equinum* infection in horses using a viable vaccine comprising a suspension of *T. equinum* material is disclosed in U.S. Pat. No. 4,229,434 to Sarkisov et al. However, there are several defects with that vaccine. First, because it is viable, the vaccine of Sarkisov et al. may cause localized infection at the injection site. Second, because the vaccine is live, it cannot be incorporated with other adjuvant materials frequently utilized in vaccines to enhance immunologic response. Finally and of most significance, there are serious concerns about the infection of handlers and other animals contacted externally with the vaccine, since the vaccine contains "live," i.e., active T. equinum. For that reason, the vaccine has not been approved for use in certain European countries and the United States.

In addition, U.S. Pat. No. 4,368,191 to Sarkisov et al. discloses a vaccine for the prophylaxis and treatment of trichophytosis caused by *T. mentagrophytes*. The patent mentions the risks to humans associated with the study and use of a vaccine comprising live, virulent T. gypseum (i.e., a variety of *T. mentagrophytes*). It attempts to overcome these health risks by using a vaccine of live *T. gypseum* of a specific strain with "weak virulence."

The live vaccine disclosed in this Sarkisov et al. patent is limited to the prophylaxis from infection by the homologous dermatophyte on which the vaccine is based. No cross-immunity or resistance to infection from other dermatophytes is disclosed.

At the present time, there is no known broad spectrum vaccine for prophylaxis of a variety of dermatophyte infections in dogs, cats, livestock and fur-bearing animals which is effective and does not pose a risk of infection to handlers and animals contacted externally with the vaccine.

SUMMARY OF THE INVENTION

An object of the present invention is to provide a vaccine for the prophylaxis of various dermatophyte infections in dogs, cats, livestock and fur-bearing animals which is safe and is inexpensive to produce.

It is a further object of this invention to provide an improved method for vaccinating dogs, cats, livestock and fur-bearing animals for maximum duration, which method is safe to both the animals and their human handlers.

A further object of the present invention is to provide an improved method of producing a vaccine for prophylaxis of dermatophyte infection in dogs, cats, livestock and furbearing animals which is economical.

With these and other objects in mind, I have now discovered that a vaccine according to the present invention can be prepared comprising a suspension of mycelial elements and spores of four "killed" dermatophytes (*T. equinum, T. mentagrophytes* (var. granulare), *M. canis* and *M. gypseum* along with an adjuvant material (i.e., immunologic stimulator) that enhances the vaccine's effectiveness.

The invention also comprises a vaccination method provided by inoculating the cat, dog or other animal with the vaccine of this invention on two occasions separated by approximately 10 days to three weeks. Additional benefits can be obtained by a further inoculation with the vaccine approximately four to six months after the second injection.

Finally, the objects of the present invention may be achieved by preparing a vaccine by isolating *T. equinum, T. mentagrophytes* (var. granulare), *M. canis* and *M. gypseum*, preparing separate suspensions of each, killing the dermatophyte strains in each suspension and combining the mycelial elements and spores of the killed strains in a single suspension which is combined with an adjuvant.

Further objects and features of the present invention may be apparent from the full specification of the invention as set forth herein.

DETAILED DESCRIPTION AND PREFERRED EMBODIMENT

A. The Vaccine

A vaccine for prophylaxis of dermatophyte infection in dogs, cats, livestock and fur-bearing animals is prepared as a suspension comprising conidia (i.e., spores) and other mycelial elements of killed *T. equinum, T. mentagrophytes* (var. granulare), *M. canis* and *M. gypseum* in an effective amount along with an adjuvant material.

The vaccine strains of the present invention were isolated from clinical cases of dermatophytosis (circumscribed areas of hair loss, scaly dermatitis and microscopic evidence of ectothrix formation) in cats, dogs, and horses. This was accomplished by plucking scales and hairs from typical lesions and inoculating them on to "C & C" medium (i.e., "Soytone" manufactured by Difco) dextrose agar containing cyclohexamide and chloramphenicol; 0.5 g. and 0.05 g. per liter, respectively). The cultures were incubated (at room temperature) until colonies of dermatophytes appeared 7 to 10 days later. Single colonies were picked and transferred to new medium and grown to assure purity of the isolate. The isolates' identity was assured by microscopic examination for typical morphology and by nutritional tests showing the presence or absence of a requirement for nicotinic acid.

*T. equinum* strain B.F. was obtained from an epidemic of dermatophyte infection on horses in Bloomfield, Nebr. This strain grows as a flat, buff to brown, granular colony with a reddish-brown reverse pigmentation. Microconidia are produced in great abundance, but macroconidia are rare. Inoculum materials corresponding to the 4th to 5th passage on laboratory media are preserved in refrigerated suspensions and in lyophilized stock cultures.

*T. mentagrophytes* (var. granulare) strain 89F6667 was isolated from a clinically-infected cat showing circumscribed areas of hair loss, scaling dermatitis and microscopic evidence of ectothrix. The culture grows as a flat, granular, buff colored colony with tannish, brown reverse pigmentation. It produces microconidia in great abundance but macroconidia are infrequent. The organism grows equally well on casein basal agar ("CBA") and CBA supplemented with nicotinic acid. The organism perforates human hair when grown in standard hair culture tests. Stock cultures corresponding to 4th to 5th passage on laboratory media are preserved by refrigerated cell suspension or by lyophilization for use as inoculums.

*M. canis* (strain Wolf) was isolated from a kitten with clinical dermatophytosis including circumscribed areas of hair loss, scaly dermatitis and microscopic evidence of ectothrix. Infected hairs had moderate fluorescence under ultraviolet light. The culture produces abundant macroconidia with prominent surface projections (vesicles) but relatively sparse microconidia. The organism grows as a flat to moderately folded, silky to cottony white surface colony with a yellow reverse pigment. The culture is identified by its pigmentation and typical morphology of its macroconidia. Stock cultures corresponding to 4th to 5th passage on laboratory media are preserved in refrigerated cell suspensions and by lyophilization for use as inoculum for culture production.

*M. gypseum* (strain 88C7075) was isolated from a dog with clinical dermatophytosis including circumscribed areas of hair loss, scaly dermatitis, and microscopic evidence of ectothrix. The organism grows as a flat granular to velvety buff to orange colored colony that becomes white and cottony with age. The organism produces abundant rough walled (vesiculate) macroconidia and numerous microconidia. It is identified by typical morphology of its macroconidia. Stock cultures corresponding to 4th to 5th passage on laboratory media are preserved in refrigerated cell suspensions or as lyophilized cultures for use as inoculum.

The dermatophyte materials used in the vaccine are killed. The suspension is standardized optically (i.e., by light transmittance) to assure reproducibility of concentration. Before inactivation, the separate dermatophyte suspensions typically contain approximately $1 \times 10^7$ colony forming units/ml. at 5% T. This approximates 4 mg. of dermatophytes/ml. Generally, either before or after inactivation, the suspensions can be optically standardized so that they have a dermatophyte concentration between approximately 2.5 and 5% T. at 540 m$\mu$.

The vaccine can contain approximately equal parts of the suspensions of each of the four component dermatophytes. Although the proportions of the four dermatophyte types can be varied s that the total dermatophyte concentration in the vaccine remains approximately the same, it is preferred that the *M. canis* and *M. gypseum* constitute approximately 35 to 50 percent of the dermatophyte material and that the *T. equinum* and *T. mentagrophytes* constitute the other 50 to 65 percent. The preferred embodiment contains 65 percent of approximately equal portions of *T. equinum* and *T. mentagrophytes* and 35 percent of approximately equal portions of *M. canis* and *M. gypseum*.

Because the dermatophyte components of the vaccine have been killed, it is possible to combine them with a commercial adjuvant. A commercial adjuvant cannot be utilized with live vaccines, such as that disclosed in the patents of Sarkisov et al., because a live dermatophyte component cannot be lyophilized with the adjuvant, and the adjuvant would interfere with the viability and stability of the live dermatophyte.

It appears that any commercial adjuvant may be used as a vehicle to suspend the "killed" dermatophyte components in the present invention. These adjuvants include a number of commercially available materials that are useful in suspending the dermatophyte component and stimulating the vaccinated animal's immune system response. Examples of acceptable adjuvants include:

(a) "Quil A" is a commercially available adjuvant manufactured by Sargent Chemical Co., Clifton, N.J. Quil A is a purified saponin extract from the bark of the Quillaja Saponaria Molina tree. It is currently used as a suspension medium in a number of large animal vaccines throughout the world, such as the vaccines utilized in the prevention of foot and mouth disease. Quil A is the preferred material for use in this invention because it is widely used, readily available and not very expensive. It also creates very stable mixtures that do not separate.

(b) "Freund's Incomplete Adjuvant" is manufactured by many biologics producers (e.g., Sigma Chemical Co., St. Louis, Mo.). It is comprised primarily of light mineral oil.

(c) A number of anhydrous lipid based materials, such as "Lipovant" (sold by Accurate Chemical and Scientific Co., Westbury, N.Y.) which consists of a peanut oil and lecithin mixture which emulsifies quite well.

(d) Aluminum hydroxide gel sold by a number of companies including Accurate Chemical and Scientific Co.

Quil A is a water soluble compound that mixes readily with the vaccine in an amount of approximately 150 mg./l. of killed dermatophyte suspension. Freund's incomplete adjuvant and aluminum hydroxide gel are mixed approximately 1:1 on a volume basis with the dermatophyte suspension, and Lipovant is used 1 ml. to 8 ml. of the suspension.

In the preferred embodiment of the invention, Quil A is used as the adjuvant. The resulting vaccine comprising killed dermatophyte material and Quil A with dermatophyte material being present in an amount of approximately 2.5 to 5% T. at 540 m$\mu$. This vaccine has proven to be effective in dosages of approximately 5.0 ml. for horses and cattle and 0.5 ml. for cats, dogs, guinea pigs and fur-bearing animals.

B. Methods of Producing the Vaccine

In general the vaccine is prepared by preparing a separate suspension of surface growth (i.e., conidia and other mycelial elements) of each of the four dermatophytes. The dermatophyte material in each of the four suspensions is killed, optically standardized and combined with 65 percent of approximately equal portions of *T. equinum* and *T. mentagrophytes* and 35 percent of approximately equal portions of *M. canis* and *M. gypseum*. The vaccine is combined with an adjuvant to stimulate an enhanced immunological response. The basic steps in preparing the vaccine of this invention are described in more detail, as follows:

1. Culture media, culture and harvest. Each dermatophyte species (*T. equinum, T. mentagrophytes* (var. granulare) *M. canis* and *M. gypseum*) is an isolate from naturally-infected, clinically-involved animal. The strains were selected for virulence, abundance of growth and harvest yield on production media. The inoculums prepared from these strains are checked for purity and are lyophilized to preserve low culture-passage status of the strains.

Trichophyton strains *T. equinum* and *T. mentagrophytes* are grown on solid medium ($M_4OY$) containing cyclohexamide, chloramphenicol and nicotinic acid (0.5 g., 0.05 g. and 0.4 mg. per liter, respectively). Microsporum species *M. canis* and *M. gypseum* are grown on $M_4OY$ agar containing rice grains, cyclohexamide, chloramphenicol and nicotinic acid (120 g., 0.5 g., 0.05 g. and 0.4 mg. per liter, respectively). The medium is dispensed into cotton stoppered flasks (250 ml. per 2-liter flasks), allowed to stand at room temp (25° to 27° C.) for one week and then inoculated with a 3 ml. suspension (10% T) of the desired vaccine strain(s). A separate flask is used for each dermatophyte strain. After 3 to 6 weeks' growth (25° to 27° C.), 100 ml. sterile phosphate buffered saline (PBS pH 7.4) is added to the flask and the surface growth (conidia and mycelium) is washed free using a sterile brush. The suspension is filtered through gauze to remove large particles. A portion of the suspension is cultured on Sabouraud's dextrose agar, on BHI blood agar, vitamin free casein basal agar ("CBA") and on CBA plus nicotinic acid to check the purity of the harvested growth. Each suspension is optically standardized (approximately 2.5% to 5% T. at 540 m$\mu$).

2. Inactivation: Each suspension is then inactivated by adding thimerosal (1:10,000). After standing 24 to 48 hours, each suspension is sedimented by centrifugation, the supernatant fluids discarded and the sedimented mycelial elements are resuspended (PBS plus thimerosal 1:10,000) and optically standardized (2.5 to 5% T at 540 m$\mu$). The standardized suspensions are sterility checked by subculture on Sabouraud's dextrose agar and BHI blood agar. After standardization and after the checks for purity and sterility have been passed, the suspensions are then combined in the proportions indicated previously.

3. Adjuvant addition: The standardized suspension is combined with an adjuvant (e.g., Quil A, 150 mg./l.), bottled in sterile vaccine vials and appropriately labeled.

C. Application of the Vaccine/Testing

In general, the vaccine should be administered in two injections given intramuscularly at 10-day to 3-week intervals. A booster dose is recommended after approximately 4 to 6 months. Doses recommended for the vaccine are:

0.5 ml. for dogs and cats
5.0 ml. for horses and cattle

Two methods have been employed for testing the potency of the vaccine: experimental challenge and delayed cutaneous hypersensitivity.

Experimental challenge: As an example of this method, two weeks after the second vaccine dose, a group (10 or more) of vaccinated guinea pigs and a similar groups of unvaccinated guinea pigs are challenged by a virulent suspension of *T. equinum* or *M. canis* (or other dermatophyte depending on the test required). Hair is plucked from an area approximately 1 cm$^2$. on the animal's back, then an area approximately 4 cm$^2$ centering over the plucked area is clipped. Inoculum (0.1 ml. of 10% T. suspension approximating 5$\times$10$^6$ cfu/ml.) is rubbed into the clipped and plucked areas (6 to 12 strokes with a sterile rubber bulb). The animals are observed periodically over a 3 to 4 week post-inoculation period for lesion development. Hairs plucked from lesions are examined microscopically for invasion of the hairshaft and/or scales by dermatophytic mycelia and for the development of ectothrix. Clinical lesions are scored 0 to 4 as follows: 0=no discernible involvement; 1=1 cm. diameter area of erythema and scales; 2=1 cm. diameter area of erythema, scales and exudative crust; 3=2 cm. or more in diameter area of erythema, scales and exudative crust; and 4=2 or more areas 2 cm. or more in diameter with erythema, scales and exudative crust. The microscopic appearance is graded from 0 to 3+ depending on: 0=no detectable hair or scale invasion; 1+ =minimal mycelial invasion of hair or scales; 2+ =mycelial invasion plus occasional ectothrix; 3+ =frequent ectothrix. The skin of the inoculated area of each animal is brushed with a sterile, natural fiber brush which is then used to inoculate C & C agar medium for fungal growth and identification. The results of vaccinated animals are compared to those from non-vaccinated, challenged control animals. The total test takes approximately 2 months from the first injection and entails use of infectious materials and subjective results.

Delayed cutaneous hypersensitivity ("DCH") skin test. This test is more rapid, does not require use of infectious materials (i.e., contagious to human handlers) and provides an objective measurement of vaccine potency. Two weeks after the second vaccination, guinea pigs (vaccinated and control groups) are skin tested with 0.1 ml. intradermal injections of skin test antigens (The skin test antigen used is grown on neopeptone dialysate medium inoculated with the specific dermatophyte strain and incubated on a rotary shaker at 37° C. for 3 weeks. The culture filtrate is preserved [thimerosal 1:10,000] and used as the skin test sensitin. These sensitins can be balanced by dilution or concentration for a desired response in sensitized animals.) Twenty-four hours after intradermal injection, the induration at the injection site is measured (calibrated calipers) and compared to the animal's normal skin thickness. The resulting difference (induration minus normal skin thickness) constitutes the hypersensitivity ("DCH") response engendered by the vaccine. The test is significant because cell mediated immune response is considered the main basis of dermatophyte immunity. This test takes approximately one month to conduct after the initial inoculation.

A number of significant benefits have been observed from the use of the vaccine of the present invention.

First, the vaccine of the present invention is safer to use than prior art materials for several reasons. One of these is that the vaccine does not permit local infection to occur at vaccination sites in immunized subjects or on the skin or hands of vaccinators. The use of killed vaccine renders such infections virtually non-existent, and none have been reported to date in the use and application of the vaccine. In addition, the vaccine does not permit survival and transmission of other infectious agents that might gain access to the preparation (e.g. bacterial or viral agents) or permit reversion to virulence of "viable, nonvirulent" fungal immunogens.

Second, controlled studies in laboratory animals show the vaccine to increase the resistance of vaccinated animals to experimental challenge infection. Field trials are currently being conducted in commercial companion animal breeders. The vaccine is designed to protect (i.e., increase resistance to infection) companion animals, livestock and fur-bearing animals against dermatophyte infection and thereby decrease zoonotic infection exposure to their human attendants. The vaccine of this invention has a broader antigenic base than the prior art vaccines discussed previously by virtue of its containing four species of common zoophilic dermatophytes. This broader antigenic base and the antigenic cross protection between dermatophyte genera and species increases resistance in vaccinated animals to all common zoophilic dermatophytes tested.

D. Specific Examples

Example 1—Cell Mediated Immunity in Guinea Pigs

Immunity to dermatophytosis is largely due to responses of the animal's cell mediated immune ("CMI") system. The delayed cutaneous hypersensitivity ("DCH") response is a reliable, safe and objective measure of acquired CMI response to dermatophyte vaccine. The DCH response is elicited by injection of culture filtrate (neopeptone dialysate medium) antigens of separate dermatophytes intradermally and measuring the cutaneous induration with calipers 24 hours after the test injection. The induration of vaccinated animals is compared to that of similarly tested nonvaccinates.

In a typical test 10 guinea pigs were vaccinated intramuscularly twice (0.5 ml. per dose) at a 14 day interval. The vaccine comprised 2.5% T. suspension of dermatophyte material comprising 65 percent of approximately equal portions of *T. equinum* and *T. mentagrophytes* and 35 percent of approximately equal portions of *M. canis* and *M. gypseum*. The suspension was combined with Quil A adjuvant as discussed previously. Two weeks after the last vaccine dose was administered the guinea pigs were skin tested for DCH using neopeptone dialysate culture filtrate antigens of *M. canis* and *T. equinum*. The results demonstrated 2.5 to 5 times the DCH response in vaccinated animals to skin test antigens of *M. canis* and *T. equinum* as did a similar group of non vaccinated animals (2.1 and 2.2 mm. respectively in vaccinates; 0.4 and 0.8 mm. respectively in non-vaccinates).

Example 2—Challenge in Guinea Pigs

Vaccinated animals were also challenged with viable, virulent dermatophyte culture (*M. canis*) by applying culture suspensions containing approximately. $0.5 \times 10^5$ cfu/ml. to clipped areas of skin with rubbing. Two to three weeks after challenge inoculation the sites were examined for physical signs of infection; the lesions were scored numerically as described previously and hairs and scales were plucked from the lesions and examined microscopically and culturally for infection. Typically 70 percent or more of the vaccinates were protected from infection and have a lower clinical lesion score and lower hair invasion score than controls. (0=no invasion; 1=occasional scale invasion and endothrix in hairs; 2=scale invasion and ectothrix in 1 or 2 hairs; and 3=frequent and extensive ectothrix) Clinical lesion scores and hair invasion scores of vaccinates are typically 50% or more reduced below those of non-vaccinates (e.g., clinical lesion scores of 1.2 for vaccinates as compared to 2.6 for non-vaccinates and hair invasion scores of 0.8 for vaccinates compared to 2.1 for non-vaccinates).

Example 3—Commercial Catteries

Cats in commercial catteries infected with *M. canis* were vaccinated twice (0.5 ml. per dose) with booster injection at 4 to 6 months. The vaccinated cats were challenged by contact with infected cats and the contaminated premises. Cats were observed monthly for clinical manifestations of ringworm. Vaccinated cats demonstrated a reduction of approximately 70% in new infections in the few months following inauguration of vaccination. All evidence indicates a substantial and effective immunity to dermatophytes is acquired with the use of the vaccine.

I claim:

1. A vaccine for the prophylaxis of *M. canis* in cats which provides detectable cross-immunity to other dermatophyte pathogens and which poses minimum risk of infection to man and other animals exposed to the vaccine comprising a suspension of killed dermatophytes of *T. equinum*, *T. mentagrophytes* (var. granulare), *M. canis* and *M. gypseum* in an effective amount combined with an adjuvant.

2. The vaccine according to claim 1 in which the killed dermatophytes are present in an amount of 2.5 to 5% light transmittance at 540 m$\mu$.

3. The vaccine according to claim 2 in which the *T. equinum* and *T. mentagrophytes* constitute 50 to 65 percent of the killed dermatophytes.

4. The vaccine according to claim 3 in which the adjuvant is selected from the group consisting of Quil A, Freund's Incomplete Adjuvant, anhydrous lipids and aluminum hydroxide.

5. The vaccine according to claim 3 in which the adjuvant is Quil A.

6. A process for the prophylaxis of *M. canis* in cats which provides detectable cross-immunity to other dermatophyte pathogens and which poses minimum risk of infection to man and other animals exposed to the vaccine comprising inoculating the animal intramuscularly with a first inoculation at 0.5 ml. of a vaccine as claimed in claims 1, 2, 3, 4 or 5, and 10 days to three weeks after the first inoculation, inoculating the animal with a second inoculation of the same amount of said vaccine.

7. The process according to claim 6 containing the additional step of a third intramuscular inoculation of the same amount of said vaccine administered four to six months after the first and second inoculations.

* * * * *